(12) United States Patent
Komine

(10) Patent No.: US 9,677,982 B2
(45) Date of Patent: Jun. 13, 2017

(54) JIG MOUNTING DEVICE FOR MATERIAL TESTING MACHINE

(71) Applicant: SHIMADZU CORPORATION, Kyoto-shi, Kyoto (JP)

(72) Inventor: Noriaki Komine, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 14/904,812

(22) PCT Filed: Aug. 7, 2013

(86) PCT No.: PCT/JP2013/071380
§ 371 (c)(1),
(2) Date: Jan. 13, 2016

(87) PCT Pub. No.: WO2015/019446
PCT Pub. Date: Feb. 12, 2015

(65) Prior Publication Data
US 2016/0161380 A1 Jun. 9, 2016

(51) Int. Cl.
*G01N 3/08* (2006.01)
*G01N 3/04* (2006.01)

(52) U.S. Cl.
CPC ............ *G01N 3/08* (2013.01); *G01N 3/04* (2013.01); *G01N 2203/04* (2013.01); *G01N 2203/0447* (2013.01)

(58) Field of Classification Search
CPC ........ G01N 3/08; G01N 3/04; G01N 2203/04; G01N 2203/0447
USPC .......................................... 73/760, 818, 826
See application file for complete search history.

(56) References Cited

U.S. PATENT DOCUMENTS

| | | | | |
|---|---|---|---|---|
| 4,537,082 A * | 8/1985 | Meline | ...................... | G01N 3/06 33/787 |
| 5,205,080 A * | 4/1993 | Ibe | .......................... | B23B 23/02 269/21 |
| 5,219,376 A * | 6/1993 | Vinohradsky | ............ | B23H 7/26 219/69.11 |
| 5,948,994 A * | 9/1999 | Jen | .......................... | G01N 3/08 73/796 |
| 7,784,355 B2 * | 8/2010 | Kawano | .................. | G01N 3/32 73/760 |

FOREIGN PATENT DOCUMENTS

| | | |
|---|---|---|
| JP | 9-54028 A | 2/1997 |
| JP | 2008-196880 A | 8/2008 |

OTHER PUBLICATIONS

International Search Report of PCT/JP2013/071380 dated Sep. 17, 2013.

* cited by examiner

*Primary Examiner* — Max Noori
(74) *Attorney, Agent, or Firm* — Sughrue Mion, PLLC

(57) ABSTRACT

When mounting a grip 10 on a cross head 73, a pin 62 and an adapter 50 are removed from a joint 40. Then, a boss 13 of the grip 10 is inserted into a hollow part 45 of the joint 40, and the pin 62 is inserted into a through-hole 14 formed in the boss 13 of the grip 10 and a hole part 42 formed in a tubular body 41 of the joint 40. When mounting a platen 30 on the cross head 73, the adapter 50 is mounted on the joint 40. In addition, the platen 30 is mounted on the adapter 50. Further, a set screw is inserted into a hole part 52 of the adapter 50.

6 Claims, 6 Drawing Sheets

JIG MOUNTING DEVICE FOR MATERIAL TESTING MACHINE

CROSS REFERENCE TO RELATED APPLICATIONS

This application is a National Stage of International Application No. PCT/JP2013/071380 filed Aug. 7, 2013, the contents of which are incorporated herein by reference in their entirety.

TECHNICAL FIELD

The present invention relates to a jig mounting device for a material testing machine, which is capable of selectively mounting a grip for gripping a test piece when performing a tensile test or a pressing member for pressing a test piece when performing a compression test in a material testing machine capable of performing both the tensile test and the compression test. Note that the term "compression test" herein means various types of tests that apply compression force to a test piece, and is a concept including a bending test that applies compression force causing a test piece to bend.

BACKGROUND ART

In a material testing machine capable of performing both a tensile test and a compression test, it is necessary to be able to, on a crosshead, selectively mount a grip, which is a jig used to grip a test piece when performing the tensile test, or a platen, which is a jig used to press a test piece when performing the compression test.

In a conventional material testing machine, a jig mounting device for mounting a grip on a crosshead, and a jig mounting device for mounting a platen on the crosshead are separately prepared, and depending on the content of a test, these jig mounting devices are selectively used. For this reason, when changing a test method from a tensile test method to a compression test method, or from the compression test method to the tensile test method, it is necessary to replace a jig mounting device itself, causing the problems that troublesome work is required and the replacement takes time.

On the other hand, there is proposed a material testing machine including: a load cell that is connected with a grip or a platen through a jig mounting device; a holding member that holds the load cell; and a driving mechanism that applies a load to a test piece between the holding member and a table by moving up or down the holding member, in which the jig mounting device has pin-connected upper and lower members respectively functioning as universal joints, and the upper member is provided with a mounting part for the platen (see Patent Literature 1).

FIG. 5 is a schematic diagram of the conventional jig mounting device described in Patent Literature 1.

In this jig mounting device, the load cell 101 is placed on the upper surface of a crosshead 102 coaxially with a through-hole opening in the crosshead 102. In addition, a screw rod 103 penetrates through the through-hole and the load cell 101, and the load cell 101 is fixed to the screw rod 103 by the action of a lock nut 104 screwed with a screw part formed in a head part of the screw rod 103.

The lower end part of the screw rod 103 is connected with a fork part 105. In the fork part 105, a pin hole insertable with a pin 106 is formed. When mounting a grip (illustration is omitted) for gripping a test piece on the jig mounting device, the grip is mounted on the fork part 105 by inserting a head part formed in the grip into a concave part 107 of the fork part 105, and inserting the pin 106 into a through-hole formed in the head part of the grip. In this case, even in the case where there is a gap between the pin hole formed in the fork part 105 or the through-hole formed in the head part of the grip and the pin 106, the grip is pulled downward at the time of a tensile test, and therefore the gap does not affect the material test.

On the other hand, when mounting a platen 108 on the jig mounting device, as illustrated in FIG. 5, the platen 108 is mounted on the fork part 105 by inserting a head part of a stepped connecting rod 110 attached to a pressing part 109 of the platen 108 into the concave part 107 of the fork part 105, and inserting the pin 106 into the through-hole formed in a head part of the platen 108. Then, a male screw formed on the outer circumferential surface of a large diameter part of the stepped connecting rod 110 is screwed into a female screw formed on the inner circumferential surface of a lock nut 111. After that, by bringing the lock nut 111 into abutting contact with the fork part 105, and drawing the platen 108 toward the pin 106 side by the action of the lock nut 111, the platen 108 is fixed to the fork part 105. In doing so, even in the case where there is a gap between the pin hole formed in the fork part 105 or the through-hole formed in the head part of the stepped connecting rod 110 and the pin 106, the platen 108 can be securely fixed to the fork part 105.

CITATION LIST

Patent Literature

[Patent Literature 1]
Japanese Unexamined Patent Publication JP-A2008-196880

SUMMARY OF INVENTION

Technical Problem

The jig mounting device described in Patent Literature 1 is a superior device capable of selectively mounting the grip or the platen 108; however, a problem as described below may occur.

FIG. 6 is an enlarged view illustrating the screwing relationship between the male screw formed on the outer circumferential surface of the large diameter part of the stepped connecting rod 110 and the female screw formed on the inner circumferential surface of the lock nut 111 in the state illustrated in FIG. 5.

The jig mounting device illustrated in FIG. 5 is configured to draw the platen 108 toward the pin 106 side by the action of the lock nut 111, and thereby fix the platen 108 to the fork part 105, and therefore as illustrated in FIG. 6, lower side thread faces of the male screw formed on the outer circumferential surface of the large diameter part of the stepped connecting rod 110 and corresponding ones of the upper side thread faces of the female screw formed on the inner circumferential surface of the lock nut 111 are in abutting contact with each other. That is, in this state, between upper side thread faces of the male screw formed on the outer circumferential surface of the large diameter part of the stepped connecting rod 110 and corresponding ones of the lower side thread faces of the female screw formed on the inner circumferential surface of the lock nut 111, there are gaps.

When pressing a test piece with the platen 108 in order to perform a compression test, upward force acts on the platen 108. For this reason, the force attempting to move the stepped connecting rod 110 upward moves the platen 108 in a direction making it possible to eliminate the gaps formed between the upper side thread faces of the male screw formed on the outer circumferential surface of the large diameter part of the stepped connecting rod 110 and corresponding ones of the lower side thread faces of the female screw formed on the inner circumferential surface of the lock nut 111. For this reason, the relationship between test force and displacement becomes discontinuous, and thereby the compression test cannot be accurately performed.

The present invention is made in order to solve the above-described problem, and intends to provide a jig mounting device for a material testing machine, which is capable of selectively mounting a grip or a pressing member, and makes it possible to accurately perform a compression test.

Solution to Problem

A first aspect of the present invention is a jig mounting device for a material testing machine, which is capable of selectively mounting a grip for gripping a test piece when performing a tensile test or a pressing member for pressing a test piece when performing a compression test, and the jig mounting device includes: a joint in which a hollow part insertable with a boss of the grip, and a hole part insertable with a pin penetrating through a through-hole formed in the boss of the grip in a state where the boss of the grip is inserted into the hollow part are formed; an adapter including a hollow part insertable with a boss of the pressing member; and a pressing member fixing member for fixing the pressing member to the adapter in a state where the boss of the pressing member is inserted into the hollow part of the adapter and the adapter and the pressing member are in surface contact with each other, and includes an adapter fixing mechanism adapted to bring the joint and the adapter into surface contact with each other and fix the adapter to the joint.

A second aspect of the present invention is the first aspect of the present invention in which the adapter fixing mechanism is a male screw that is formed in the joint and screwed into a female screw formed in the adapter.

A third aspect of the present invention is the first aspect of the present invention in which the pressing member fixing member is a set screw that presses the boss of the pressing member.

A fourth aspect of the present invention is the third aspect of the present invention in which an outer circumferential part of the boss of the pressing member is formed with a groove part insertable with a head part of the set screw.

A fifth aspect of the present invention is a jig mounting device for a material testing machine, which is capable of selectively mounting a grip for gripping a test piece when performing a tensile test or a pressing member for pressing a test piece when performing a compression test, and the jig mounting device includes: a joint that has a tubular body formed with a hollow part insertable with a boss of the grip, in which the tubular body is formed with a hole part insertable with a pin penetrating through a through-hole formed in the boss of the grip in a state where the boss of the grip is inserted thereinto, and formed with a female screw on an inner wall thereof; an adapter that has a flange part and a hollow part insertable with a boss of the pressing member, and is formed in an outer circumferential part thereof with a male screw screwable with the female screw formed on the inner wall of the tubular body of the joint; and a pressing member fixing member for fixing the pressing member to the adapter in a state where the boss of the pressing member is inserted into the hollow part of the joint and the adapter and the pressing member are in surface contact with each other, wherein in a state where the female screw of the joint and the male screw of the adapter are screwed together, a lower surface of the tubular body of the joint and an upper surface of the flange part of the adapter are in surface contact with each other.

A sixth aspect of the present invention is the fifth aspect of the present invention in which the boss of the pressing member has a cylindrical shape, and an outer circumferential part thereof is formed with a groove part; the adapter is formed with a hole part from the outer circumferential part to the hollow part thereof; and the pressing member fixing member is a set screw that passes through the hole part of the adapter and penetrates into the groove part formed in the boss of the pressing member.

Advantageous Effects of Invention

According to the first and fifth aspects of the present invention, by mounting/dismounting the adapter on/from the joint, the grip or the pressing member can be easily selected and mounted. When doing so, since the joint and the adapter are in surface contact with each other, and the adapter and the pressing member are surface contact with each other, the positional relationship among the joint, the adapter, and the pressing member can be kept constant, and therefore the compression test can be accurately performed.

According to the second aspect of the present invention, the adapter can be easily fixed to the joint.

According to the third aspect of the present invention, the pressing member can be easily fixed to the adapter by the set screw.

According to the fourth and sixth aspects of the present invention, regardless of a rotation angle position of the pressing member, the pressing member can be fixed to the adapter by the action of the groove part.

DESCRIPTION OF EMBODIMENTS

Figure 1:
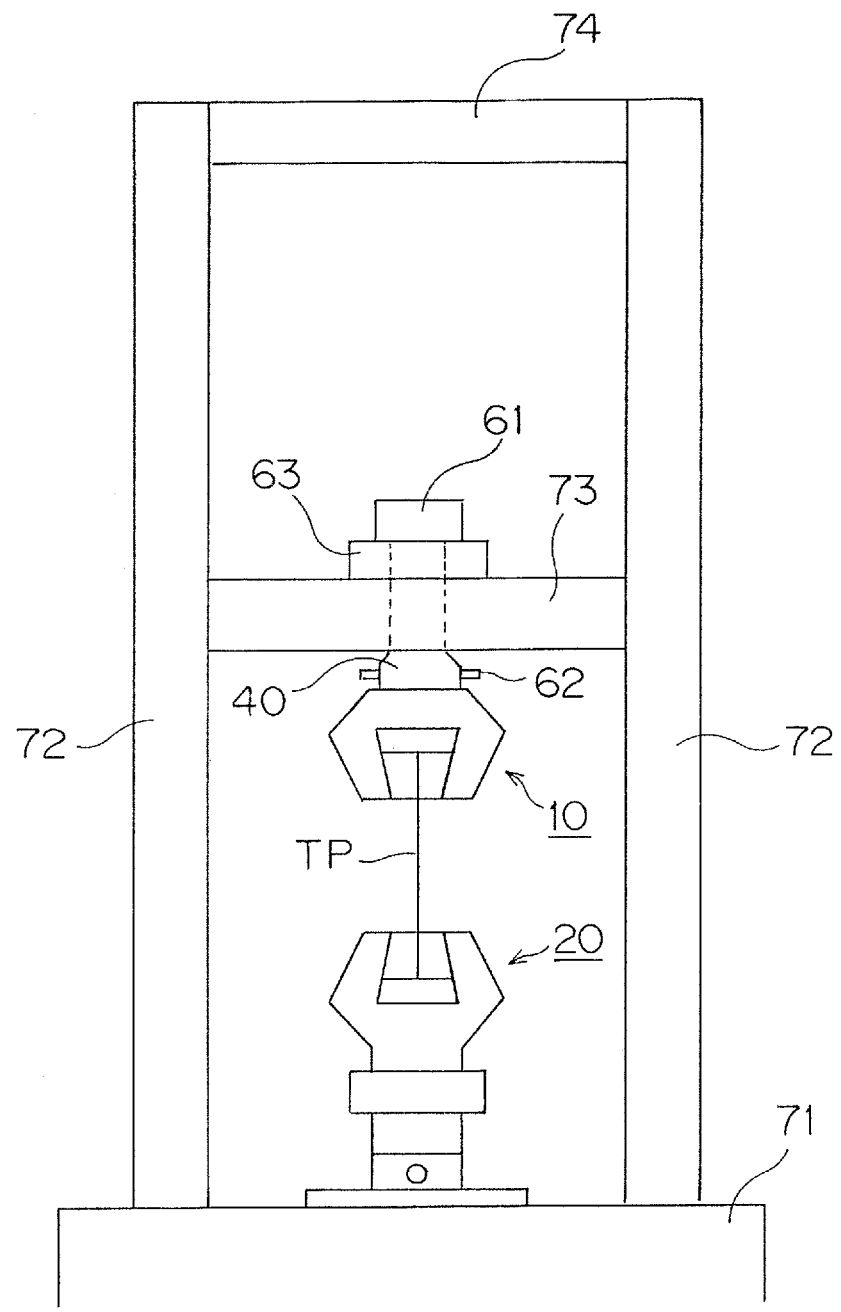
FIG. 1 is a schematic diagram of a material testing machine applied with a jig mounting device according to the present invention.

In the following, an embodiment of the present invention will be described on the basis of drawings. First, the configuration of a material testing machine applied with a jig mounting device according to the present invention will be described. FIG. 1 is a schematic diagram of the material testing machine applied with the jig mounting device according to the present invention. Note that FIG. 1 illustrates a state where a pair of grips 10 and 20 is mounted in the material testing machine in order to perform a tensile test on a test piece TP.

This material testing machine includes: a pair of support posts 72 installed upright on a table 71; and a cross yoke 74 connecting the upper parts of the support posts 72. Inside the respective support posts 72, screw rods of which illustration is omitted are disposed. The respective screw rods are rotated in synchronization with each other by driving of a motor of which illustration is omitted. Also, the material testing machine includes a cross head 73 capable of moving up or down along the pair of support posts 72. In both end parts of the cross head 73, nuts are provided, and screwed with the pair of screw rods. For this reason, the pair of screw rods rotates in synchronization with each other, and thereby the cross head 73 moves up or down.

On the lower surface of the cross head 73, the grip 10 for gripping the upper end of the test piece TP is fixed through the below-described joint 40. By the action of a lock nut 61, the joint 40 is connected to a load cell 63 fixed on the upper surface side of the cross head 73. Also, on the table 71, the grip 20 for gripping the lower end of the test piece TP is disposed.

Note that when performing a compression test on a test piece, the below-described platen 30 as a pressing member is mounted in place of the upper grip 10. Also, when performing the compression test on the test piece, a supporting member for placing the test piece to be subjected to a compression test is mounted in place of the lower grip 20.

Figure 2:
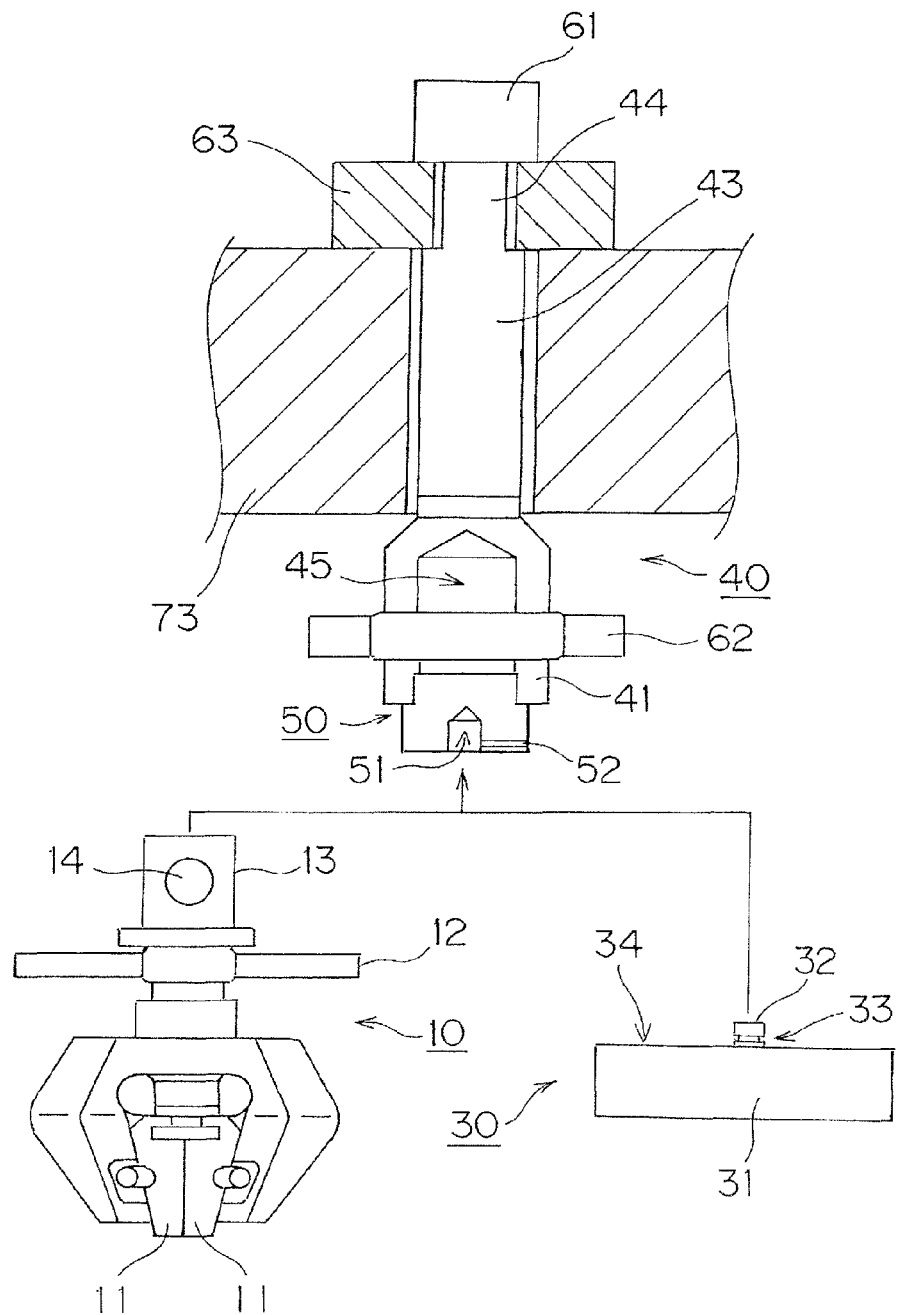
FIG. 2 is a schematic diagram of the jig mounting device according to the present invention.
Figure 3:
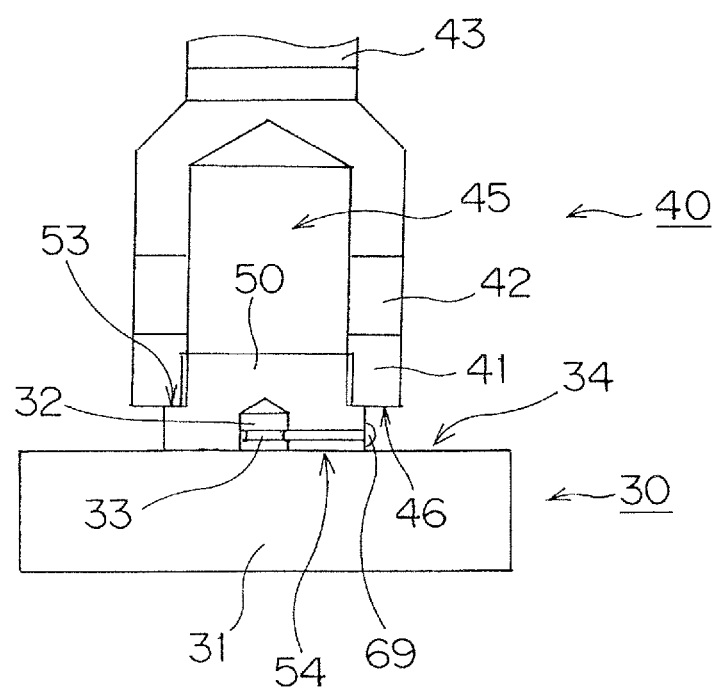
FIG. 3 is a side view illustrating a state where the platen 30 is mounted on the joint 40 through the adapter 50.
Figure 4:
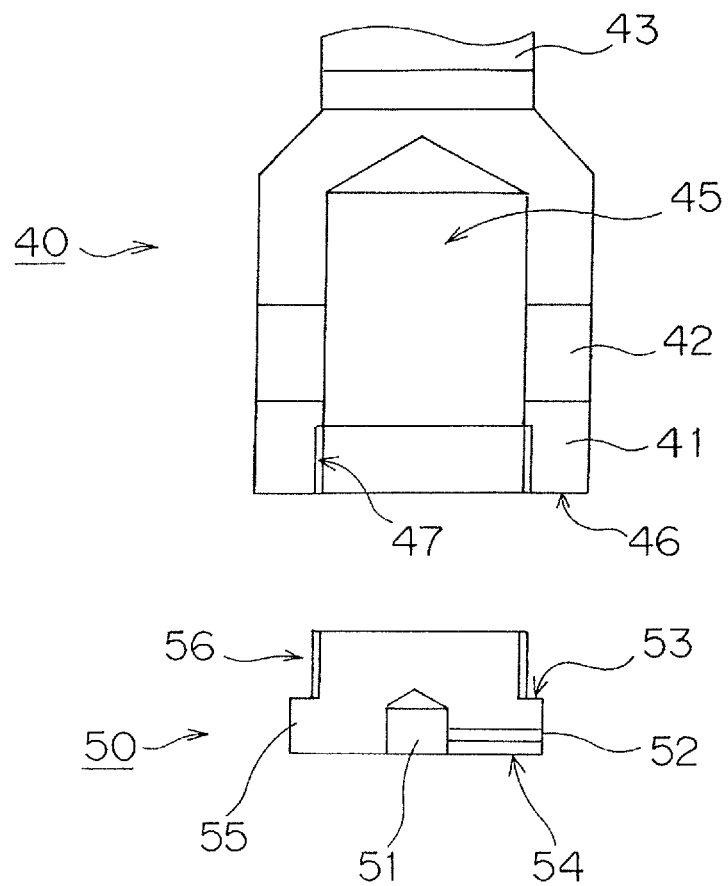
FIG. 4 is a side view illustrating the joint 40 and the adapter 50.
Figure 5:
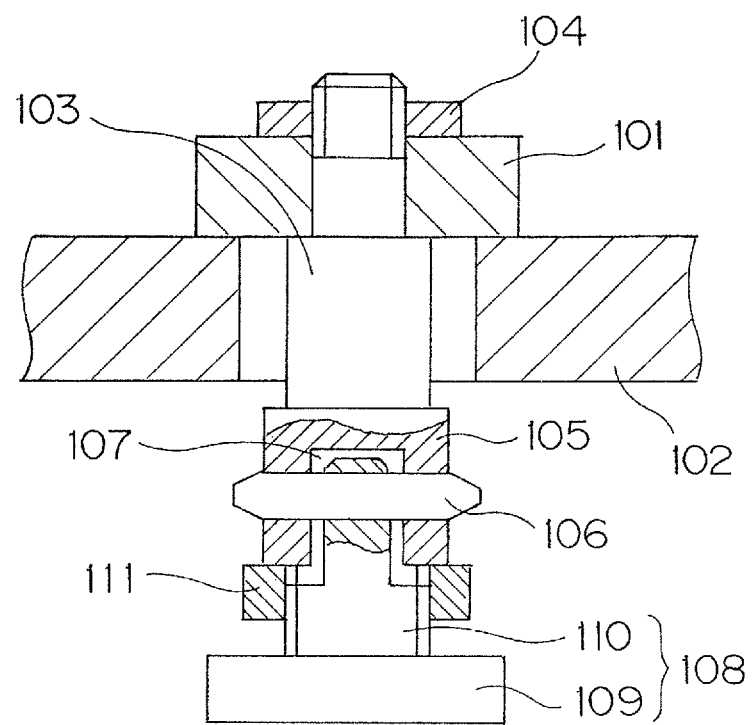
FIG. 5 is a schematic diagram of a conventional jig mounting device.
Figure 6:
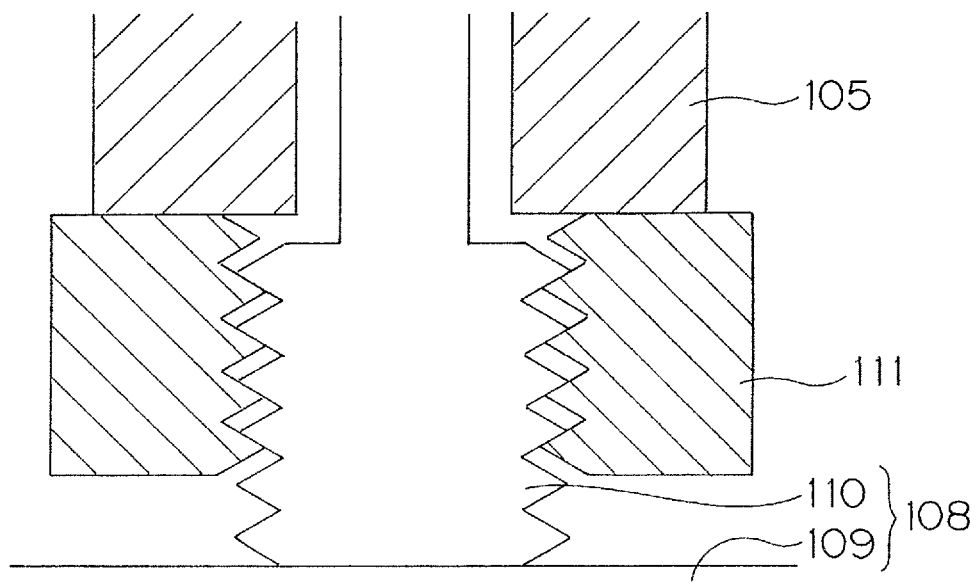
FIG. 6 is an enlarged view illustrating the screwing relationship between a male screw formed on the outer circumferential surface of a large diameter part of a stepped connecting rod 110 and a female screw formed on the inner circumferential surface of a lock nut 111.

Next, the configuration of the jig mounting device for the material testing machine according to the present invention will be described. FIG. 2 is a schematic diagram of the jig mounting device according to the present invention. Also, FIG. 3 is a side view illustrating a state where the platen 30 is mounted on the joint 40 illustrated in FIG. 2 through an adapter 50. Further, FIG. 4 is a side view illustrating the joint 40 and the adapter 50. Note that in FIGS. 3 and 4, only part of the joint 40 is illustrated.

This jig mounting device for the material testing machine is one for making it possible to, on the cross head 73, selectively mount the grip 10 used at the time of the tensile test or the platen 30 used at the time of the compression test, and includes the joint 40 and the adapter 50.

The grip 10 is one also referred to as a gripper, and a jig used when performing the tensile test. The grip 10 includes: a pair of gripping teeth 11 for gripping the test piece TP illustrated in FIG. 1; a lever 12 for performing an open/close operation of the gripping teeth 11; and a boss 13. In the boss 13, a through-hole 14 allowing the below-described pin 62 to penetrate through is formed. In addition, the grip 20 illustrated in FIG. 1 also has almost the same configuration as that of the grip 10.

On the other hand, the platen 30 is one that functions as the pressing member according to the present invention, and a jig used when performing the compression test. The platen 30 is configured to include: a pressing part 31 for pressing the test piece to be subjected to the compression test; and a boss 32 attached to the pressing part 31. The upper surface of the pressing part 31 is processed into a flat surface 34. Also, on the outer circumferential surface of the boss 32, a groove part 33 is formed.

The joint 40 includes: a tubular body 41 formed with a hollow part 45 insertable with the boss 13 of the grip 10; a connecting part 43, and a screw part 44. As illustrated in FIG. 2, the connecting part 43 of the joint 40 penetrates through a hole part drilled in the cross head 73, and the screw part 44 penetrates through a hole part of the load cell 63. Also, the load cell 63 is connected to the upper part of the joint 40 by the action of the lock nut 61 screwed with the screw part 44 of the joint 40.

Inside the tubular body 41 of the joint 40, a hole part 42 insertable with a pin 62 penetrating through the through-hole 14 formed in the boss 13 in a state where the boss 13 of the grip 10 is inserted is formed. Also, on the inner wall of the tubular body 41, a female screw 47 is formed. The female screw 47 is adapted to be screwable with the below-described male screw 56 formed in the outer circumferential part of the adapter 50. Further, the lower surface of the tubular body 41 is processed into a flat surface 46.

The adapter 50 has: a flange part 55; and a hollow part 51 insertable with the boss 32 of the platen 30 in the center of the flange part 55. The outer circumferential part above the flange part 55 of the adapter 50 is formed with the male screw 56 screwable into the above-described female screw 47 formed on the inner wall of the tubular body 41 of the joint 40. The upper surface of the flange part 55 of the adapter 50 is processed into a flat surface 53. Also, the lower surface of the adapter 50 is processed into a flat surface 54 as well. Further, in the flange part 55 of the adapter 50, a hole part 52 extending from the outer circumferential part of the flange part 55 to the hollow part 51 is formed.

When mounting the grip 10 on the cross head 73 of the material testing machine in order to perform the tensile test, the pin 62 and the adapter 50 are removed from the joint 40 in the state illustrated in FIG. 2 in the jig mounting device for the material testing machine having such a configuration. Then, the boss 13 of the grip 10 is inserted into the hollow part 45 of the joint 40. When doing so, the grip 10 is rotated 90 degrees around the vertical axis from the state illustrated in FIG. 2, and thereby the through-hole 14 formed in the boss 13 of the grip 10 is arranged so as to face to the hole part 42 formed in the tubular body 41 of the joint 40. In this state, the pin 62 is inserted into the through-hole 14 formed in the boss 13 of the grip 10 and the hole part 42 formed in the tubular body 41 of the joint 40.

In doing so, the grip 10 is fixed to the load cell 63 and the cross head 73 through the joint 40. Note that in this state, even in the case where there is a gap between the hole part 42 formed in the tubular body 41 of the joint 40 or the through-hole 14 formed in the boss 13 of the grip 10, and the pin 62, the gap does not affect the material test because the grip 10 is pulled downward at the time of the tensile test.

On the other hand, when mounting the platen 30 on the cross head 73 of the material testing machine in order to perform the compression test, the pin 62 is removed from the joint 40 in the state illustrated in FIG. 2 in the jig mounting device for the material testing machine. When doing so, to describe the relationship between the joint 40 and the adapter 50, the adapter 50 is mounted on the joint 40 by screwing together the female screw 47 formed on the inner wall of the tubular body 41 of the joint 40 and the male screw 56 formed in the outer circumferential part of the adapter 50. In this state, the flat surface 46 as the lower surface of the tubular body 41 of the joint 40 and the flat surface 53 as the upper surface of the flange part 55 of the adapter 50 are in surface contact with each other. For this reason, the adapter 50 and the joint 40 are positioned having a constant positional relationship.

Subsequently, the platen 30 is mounted on the adapter 50. When doing so, the boss 32 of the platen 30 is inserted into the hollow part 51 of the adapter 50. Then, a set screw 69 is inserted into the hole part 52 that is formed in the flange part 55 of the adapter 50 from the outer circumferential part to the hollow part 51. The set screw 69 passes through the hole part 52, and the head part of the set screw 69 penetrates into the groove part 33 formed in the outer circumferential part of the boss 32 of the platen 30. In doing so, the platen 30 is fixed to the adapter 50. Note that the groove part 33 formed in the outer circumferential part of the boss 32 of the platen 30 is formed throughout the entire circumference of the outer circumferential part of the boss 32, and therefore even in the case where the platen 30 is arranged in any rotation angle position, the platen 30 can be fixed to the adapter 50.

In this state, the platen 30 is fixed to the adapter 50 with the flat surface 54 as the lower surface of the adapter 50 and the flat surface 34 as the upper surface of the pressing part 31 of the platen 30 being in surface contact with each other. For this reason, the adapter 50 and the platen 30 are positioned having a constant positional relationship.

In doing so, the platen 30 is fixed to the load cell 63 and the cross head 73 through the joint 40 and the adapter 50. Note that in this state, the joint 40 and the adapter 50 are in surface contact with each other, and the adapter 50 and the platen 30 are in surface contact with each other. For this reason, the joint 40, the adapter 50, and the platen 30 can be constantly kept having a constant positional relationship. This makes it possible to accurately perform the compression test.

As described above, in the jig mounting device for the material testing machine according to the present invention, by selectively fitting the pin 62 or the adapter 50 to the joint 40 to use it depending on a material test mode, the grip 10 or the platen 30 can be selectively mounted in the material testing machine.

REFERENCE SIGNS LIST

10 Grip
11 Gripping teeth
13 Boss
14 Through-hole
20 Grip
30 Platen
31 Pressing part
32 Boss
33 Groove part
34 Flat surface
40 Joint
41 Tubular body
42 Hole part
43 Connecting part
44 Screw part
45 Hollow part
46 Flat surface
47 Female screw
50 Adapter
51 Hollow part
52 Hole part
53 Flat surface
54 Flat surface
55 Flange part
56 Male screw
61 Lock nut
62 Pin
63 Load cell
73 Cross head

The invention claimed is:

1. A jig mounting device for a material testing machine, the jig mounting device being capable of selectively mounting a grip for gripping a test piece when performing a tensile test or a pressing member for pressing a test piece when performing a compression test, the jig mounting device comprising:
a joint in which a tubular body and a hole part are formed, the tubular body formed with a hollow part insertable with a boss of the grip, and the hole part insertable with a pin penetrating through a through-hole formed in the boss of the grip in a state where the boss of the grip is inserted into the hollow part;
an adapter comprising a flange part and a hollow part, the hollow part insertable with a boss of the pressing member;
a pressing member fixing member for fixing the pressing member to the adapter in a state where the boss of the pressing member is inserted into the hollow part of the adapter, and a lower surface of the adapter and an upper surface of the pressing member are in surface contact with each other, and
an adapter fixing mechanism adapted to bring the joint and the adapter into surface contact with each other and fix the adapter to the joint.

2. The jig mounting device for a material testing machine according to claim 1, wherein
the adapter fixing mechanism is a male screw that is formed in the adapter and screwed into a female screw formed in the joint.

3. The jig mounting device for a material testing machine according to claim 1, wherein
the pressing member fixing member is a set screw that presses the boss of the pressing member.

4. The jig mounting device for a material testing machine according to claim 3, wherein
an outer circumferential part of the boss of the pressing member is formed with a groove part insertable with a head part of the set screw.

5. A jig mounting device for a material testing machine, the jig mounting device being capable of selectively mounting a grip for gripping a test piece when performing a tensile test or a pressing member for pressing a test piece when performing a compression test, the jig mounting device comprising:
a joint that has a tubular body formed with a hollow part insertable with a boss of the grip, wherein the tubular body is formed with a hole part insertable with a pin penetrating through a through-hole formed in the boss of the grip in a state where the boss of the grip is inserted thereinto, and formed with a female screw on an inner wall thereof;
an adapter that has a flange part and a hollow part insertable with a boss of the pressing member, and is formed in an outer circumferential part thereof with a male screw screwable with the female screw formed on the inner wall of the tubular body of the joint; and
a pressing member fixing member for fixing the pressing member to the adapter in a state where the boss of the pressing member is inserted into the hollow part of the adapter, and a lower surface of the adapter and an upper surface of the pressing member are in surface contact with each other, wherein
in a state where the female screw of the joint and the male screw of the adapter are screwed together, a lower surface of the tubular body of the joint and an upper surface of the flange part of the adapter are in surface contact with each other.

6. The jig mounting device for a material testing machine according to claim 5, wherein:

the boss of the pressing member has a cylindrical shape, and an outer circumferential part thereof is formed with a groove part;

the adapter is formed with a hole part from the outer circumferential part to the hollow part thereof; and the pressing member fixing member is a set screw that passes through the hole part of the adapter and penetrates into the groove part formed in the boss of the pressing member.

* * * * *